(12) United States Patent
Bonrath et al.

(10) Patent No.: US 12,139,456 B2
(45) Date of Patent: Nov. 12, 2024

(54) VITAMIN K2 SYNTHESIS

(71) Applicant: DSM IP Assets B.V., Heerlen (NL)

(72) Inventors: Werner Bonrath, Kaiseraugst (CH); Rolf Kuenzi, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 17/801,681

(22) PCT Filed: Feb. 16, 2021

(86) PCT No.: PCT/EP2021/053706
§ 371 (c)(1),
(2) Date: Aug. 23, 2022

(87) PCT Pub. No.: WO2021/170449
PCT Pub. Date: Sep. 2, 2021

(65) Prior Publication Data
US 2023/0159429 A1    May 25, 2023

(30) Foreign Application Priority Data
Feb. 25, 2020    (EP) .................................. 20159175

(51) Int. Cl.
*C07C 67/293* (2006.01)
*C07C 46/06* (2006.01)
*C07C 50/14* (2006.01)

(52) U.S. Cl.
CPC ............ *C07C 67/293* (2013.01); *C07C 46/06* (2013.01); *C07C 50/14* (2013.01)

(58) Field of Classification Search
CPC ....... C97C 67/293; C07C 69/16; C07C 69/78; C07C 46/06; C07C 50/14; B01J 31/0227
See application file for complete search history.

(56) References Cited

U.S. PATENT DOCUMENTS

| | | | |
|---|---|---|---|
| 8,815,985 B2 * | 8/2014 | Wakabayashi | C08L 83/04 524/99 |
| 2006/0052618 A1 | 3/2006 | Bonrath et al. | |
| 2007/0060761 A1 * | 3/2007 | Tomiyama | C07C 37/0555 552/299 |

FOREIGN PATENT DOCUMENTS

| | | | | |
|---|---|---|---|---|
| AU | 18731/88 | | 1/1989 | |
| CN | 1816539 | | 8/2006 | |
| CN | 102351677 | * | 2/2012 | ............ C07C 46/06 |
| CN | 104011016 | | 8/2014 | |
| CN | 104513149 | | 5/2015 | |
| CN | 104744230 | | 7/2015 | |
| CN | 105399615 | | 3/2016 | |
| GB | 768650 | | 2/1957 | |
| WO | WO 02/078623 | | 10/2002 | |
| WO | WO 2005/005407 | | 1/2005 | |
| WO | 2007/032378 | | 3/2007 | |

OTHER PUBLICATIONS

Suhara, Y. et al., Method for the determination of Vitamin K monologues in Human Plasma using high-performance liquid chromatography-tandem mass spectrometry, Analytical Chemistry, vol. 77, No. 3, pp. 752-763 (Year: 2005).*
CN102351677, Ziping Luo et al., Method for chemical synthesis of vitamin K2, English translation, 15 pages (Year: 2012).*
Suhara, Y. et al., "Method for the Determination of Vitamin K Homologues in Human Plasma Using High-Performance Liquid Chromatography—Tandem Mass Spectrometry" Feb. 1, 2005, Analytical Chemistry, vol. 77, No. 3, pp. 757-763 (7 pages).
International Search Report and Written Opinion of the ISA for PCT/EP2021/053706, dated Apr. 26, 2021 (14 pages).
The First Office Action, CN Application No. 202180016011.7, Apr. 27, 2023.
Liu Xingquan, "Research progress on the synthesis of K-series vitamin intermediate 2-methyl-1,4-napthoquinone", Chemical Technology, 2003, 11(2): 49-54.
Notice of Reasons for Rejection, JP Application No. P2022-543714, Jul. 23, 2024.

* cited by examiner

*Primary Examiner* — Yate' K Cutliff
(74) *Attorney, Agent, or Firm* — NIXON & VANDERHYE P.C.

(57) ABSTRACT

The present invention relates to a new process of production of menaquinone 4, which is also known as vitamin K2.

9 Claims, No Drawings

VITAMIN K2 SYNTHESIS

This application is the U.S. national phase of International Application No. PCT/EP2021/053706 filed Feb. 16, 2021 which designated the U.S. and claims priority to EP 20159175.7 filed Feb. 25, 2020, the entire contents of each of which are hereby incorporated by reference.

The present invention relates to a new process of production of menaquinone 4, which is also known as Vitamin K2.

Vitamin K2 or menaquinone is one of three types of vitamin K, the other two being Vitamin K1 (phylloquinone) and K3 (menadione). K2 is a bacterial product and is usually found in fermented foods or animal products, such as eggs, dairy, and meat, as well as fermented foods such as cheese and yogurt.

There are nine chemical variants of vitamin K2, determined by number of isoprenyl units in their side chains.

The most common in the human diet is the short-chain menaquinone 4 (MK-4), which is usually produced by bacterial conversion of vitamin K 1

Menaquinone 4 (MK-4) has the following chemical formula

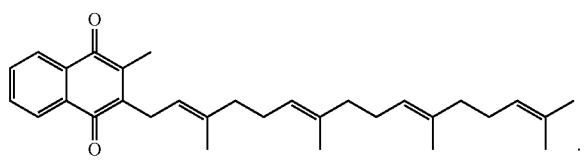

MK-4

Vitamin K2 has very interesting and important properties. It plays a role in blood clotting and wound healing.

Furthermore, vitamin K2 may lower the risk of cardiovascular damage and improve overall heart health.

Vitamin K2 promotes healthy bone mineral density by carboxylating osteocalcin, a protein that binds calcium to bones.

A 2016 study investigated the effects of vitamin K2 in rats with metabolic syndrome, high blood glucose levels and symptoms of anxiety, depression, and memory deficit.

After 10 weeks, treatment with vitamin K had normalized blood glucose and reduced symptoms of anxiety and depression.

Vitamin K2 has antioxidant properties that may help protect against cancer. In addition, findings suggest that K2 may suppress genetic processes that lead to tumor growth.

Vitamin K2 can be found in eggs, dairy, and meat, as well as fermented foods such as cheese and yogurt.

Vitamin K2 can be also be produced chemically. There are few ways known from the prior art how to produce vitamin K2. For example, from US 2007/0060761 or Kozlov, E. I., Meditsinskaya Promyshlennost SSSR (1965), 19(4), 16-21).

But the processes known from the prior art do have the unfortunate disadvantage that there are side reactions, which leads to low yield as well as a complicated separation process to get the desired product out to the reaction mixture Due to the importance of vitamin K2, there is always a need to find a new and improved process to obtain vitamin K2.

Therefore, the goal of the present invention was to find a new process to produce menaquinone 4 (or an intermediate, which can then be used in the production of menaquinone 4).

It was found that the used when starting from 4-hydroxy-2-methylnaphthalen-1-yl benzoate (compound of formula (II)) and using specific catalyst, an intermediate for the Vitamin K2 synthesis can be produced in good yields. Furthermore, the new process uses a heterogeneous catalyst, which can be separated easily in comparison to a homogenous catalyst.

The process according to the present invention relates to the production of the compound of formula (I), which is an intermediate in the menaquinone 4 production

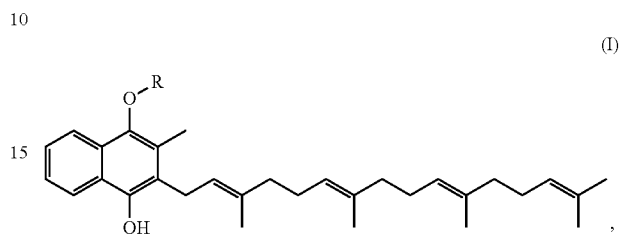

wherein R is

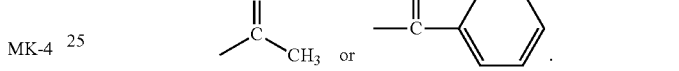

The new process according to the present invention used the compound of formula (II)

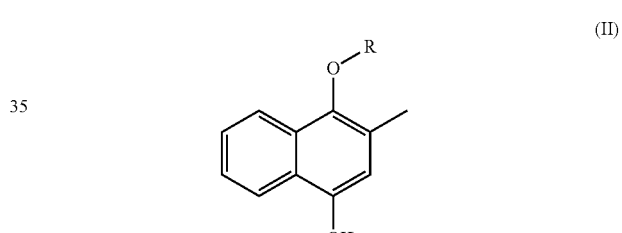

wherein R is

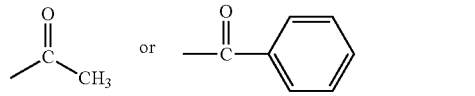

as starting material.

4-Hydroxy-2-methylnaphthalen-1-yl benzoate can be purchased commercially or it is easy to be produced (Ullmann's Encyclopedia of Industrial Chemistry, 1996, A27, 488-506).

To obtain the compound of formula (I) the compound of formula (I) is used in a condensation reaction with geranyl geraniol, which is the compound of formula (III)

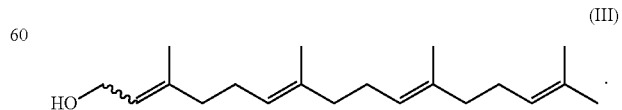

The new and improved process according to the present invention is carried out in the presence of a heterogeneous catalyst.

The heterogeneous catalyst used in the process according to the present invention is a triflate catalyst. Preferred triflate catalysts are those of formula (IV)

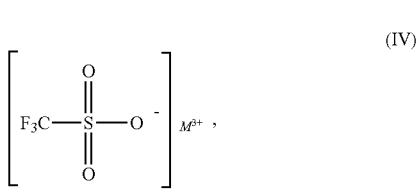

wherein M is Al, Bi or Sc.

Therefore, the present invention relates to the process (P) for the production of the compound of formula (I)

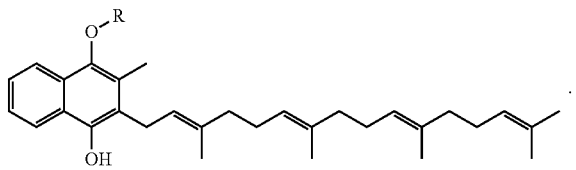

wherein R is

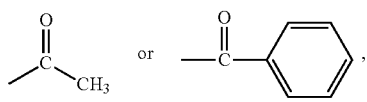

characterized in that the compound of formula (II)

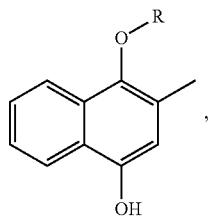

wherein R is

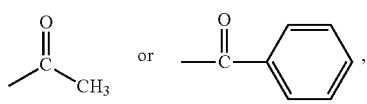

is reacted with the compound of formula (III)

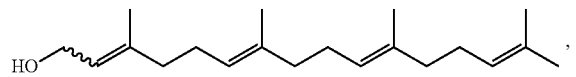

in the presence of a heterogeneous triflate catalyst.

Therefore, the present invention relates to the process (P'), which is process (P), wherein the heterogeneous catalyst is a compound of formula (IV)

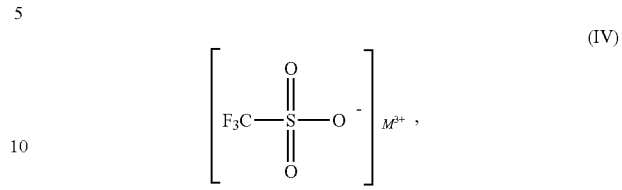

wherein M is Al, Bi or Sc.

As stated above the heterogeneous catalyst can be separated easily from the reaction mixture. Furthermore, the Al, Bi and Sc catalyst of the present invention are more effective than Zn catalyst, which are used in the prior art. Furthermore far less of the catalysts of the present invention are needed when compared to the prior art.

The process according to the present invention is usually carried out in an inert solvent-systems.

The inert solvent system can be apolar as well as polar or a mixture of such solvents. Suitable solvent systems are two-phase solvent systems with an apolar phase based on linear or branched $C_6$-$C_{12}$ aliphatic (such as 2-ethylhexane, heptane, decane or dodecane) and a polar phase based on ethylene carbonate or propylene carbonate (or a mixture of ethylene carbonate and propylene carbonate (usually 1:1 mixture)).

Therefore, the present invention relates to the process (P1), which is process (P) or (P'), wherein the process is carried out in an inert solvent system.

Therefore, the present invention relates to the process (P1'), which is process (P1), wherein the solvent system is two-phase solvent system with an apolar phase based on linear or branched $C_6$-$C_{12}$ aliphates (such as 2-ethylhexane, heptane, decane or dodecane) and a polar phase based on ethylene carbonate or propylene carbonate (or a mixture of ethylene carbonate and propylene carbonate (usually 1:1 mixture)).

Therefore, the present invention relates to the process (P1"), which is process (P1) or (P1'), wherein the apolar solvent is chosen from the group consisting of 2-ethylhexane, heptane, decane and dodecane and the polar solvent is chosen from the group consisting of ethylene carbonate an propylene carbonate.

The process according to the present invention is usually carried out at elevated temperatures.

Usually, the process according to the present invention is carried out at a temperature of 30° C. to 150° C., preferably 50° C.-120° C.

Therefore, the present invention relates to the process (P2), which is process (P), (P'), (P1), (P1') or (P1"), wherein the process is carried out at elevated temperatures.

Therefore, the present invention relates to the process (P2'), which is process (P), (P'), (P1), (P1') or (P1") wherein the process is carried out at a temperature of 30° C. to 150° C.

Therefore, the present invention relates to the process (P2"), which is process (P), (P'), (P1), (P1') or (P1") wherein the process is carried out at a temperature of 50° C.-120° C.

The process according to the present invention is usually carried out under ambient pressure.

Therefore, the present invention relates to the process (P3), which is process (P), (P'), (P1), (P1'), (P1"), (P2), (P2') or (P2"), wherein the process is carried out under ambient pressure.

In the process according to the present invention the compound of formula (II) and the compound of formula (III) can be used in an equimolar amount.

It is also possible that one of the starting materials (the compound of formula (II) and the compound of formula (III)) can be used in excess. In such a case, it is possible to use up to two times (mol equivalent) of one of the starting materials.

This means that the molar ratio of the compound of formula (II) to the compound of formula (III) can be 1:2 to 2:1, preferably, 1:1.5 to 1.5:1

Therefore, the present invention relates to the process (P4), which is process (P), (P'), (P1), (P1'), (P1"), (P2), (P2'), (P2") or (P3), wherein the compound of formula (II) and the compound of formula (III) are used an equimolar amount.

Therefore, the present invention relates to the process (P4'), which is process (P), (P'), (P1), (P1'), (P1"), (P2), (P2'), (P2") or (P3), wherein the molar ratio of the compound of formula (II) to the compound of formula (III) is 1:2 to 2:1.

Therefore, the present invention relates to the process (P4"), which is process (P), (P'), (P1), (P1'), (P1"), (P2), (P2'), (P2") or (P3), wherein the molar ratio of the compound of formula (II) to the compound of formula (III) is 1:1.5 to 1.5:1.

The catalyst (compound of formula (IV)) according to the present invention is used in catalytic amounts.

The substrate to catalyst ratio is from 2000:1 to 50000:1, preferably 1500:1 to 30000:1. This ratio is based on the molar amount of the compound of formula (II) to the catalyst of formula (IV).

Therefore, the present invention relates to the process (P5), which is process (P), (P'), (P1), (P1'), (P1"), (P2), (P2'), (P2"), (P3), (P4), (P4') or (P4"), wherein the substrate to catalyst ratio (based on the molar amount of the compound of formula (II) to the catalyst of formula (IV)) is from 2000:1 to 50000:1.

Therefore, the present invention relates to the process (P5'), which is process (P5), wherein the substrate to catalyst ratio (based on the molar amount of the compound of formula (II) to the catalyst of formula (IV)) is from 1500:1 to 30000:1.

The process according to the present invention can be carried out under an inert gas atmosphere. The inert can be any commonly used inert gas (or mixture thereof).

Suitable gases are $N_2$ or argon.

Therefore, the present invention relates to the process (P6), which is process (P), (P'), (P1), (P1'), (P1"), (P2), (P2'), (P2"), (P3), (P4), (P4'). (P4"), (P5) or (P5'), wherein the process is carried out under an inert gas atmosphere.

Therefore, the present invention relates to the process (P6'), which is process (P6), wherein the inert gas is chosen from the group consisting of $N_2$ or argon.

The obtained product of formula (I) can be isolated or reaction mixture (after the reaction has finished) to produce vitamin K2.

The way how to obtain vitamin K2 from the compound of formula (I) is known from the prior at.

To obtain vitamin K2, the compound of formula (I) is oxidized after saponification. The saponification can be carried out with NaOH (aq) and the oxidation can be carried out with oxygen.

The following examples serve to illustrate the invention.

EXAMPLES

Example 1

In a 100 ml flask equipped with a stirrer, an Argon inlet, a dosage inlet, water separator with a water cooled intensive condenser and a bubble counter, 4.22 g (99%, 15 mMol, 1.5 eq) of menadiol-1-benzoate together with 12 g ethylene carbonate, 15 ml n-heptane and 0.949 mg (99.9%, 2.0 μMol, 0.0002 eq) of $Al(OTf)_3$ were weighed in. Further ~10 ml n-heptane were placed in the separator. Under strong stirring (~1000 rpm) at 100° C., the dosage of 3.23 g (90%, 10 mMol, 1 eq) geranyl geraniol solved in ~2 ml n-heptane over 2 hours was started.

At the same temperature 30 minutes was stirred, then cooled down to 80° C. and add 15 ml n-heptane. The reaction mixture was placed in a separating funnel and separate the lower ethylene carbonate phase.

The organic phase is concentrated on a rotary evaporator at 40° C. to 17 mbar and degassed for 30 minutes at high vacuum to <0.1 mbar at 40° C.

The product (compound of formula (I)) was obtained in 52.5% yield (conversion >99%, selectivity 0.52).

Example 2

In a 100 ml flask equipped with a stirrer, an Argon inlet, dosage inlet, water separator with a water cooled intensive condenser and a bubble counter, 4.22 g (99%, 15 mMol, 1.5 eq) of menadiol-1-benzoate together with 12 g ethylene carbonate, 15 ml n-heptane and 1.326 mg (99.9%, 2.0 μMol, 0.0002 eq) of $Bi(OTf)_3$ were weighed in. Further ~10 ml n-heptane were placed in the separator. Under strong stirring (~1000 rpm) at 100° C., the dosage of 3.23 g (90%, 10 mMol, 1 eq) geranyl geraniol solved in ~2 ml n-heptane over 2 hours was started.

At the same temperature 30 minutes was stirred, then cooled down to 80° C. and add 15 ml n-heptane. The reaction mixture was placed in a separating funnel and separate the lower ethylene carbonate phase. The organic phase is concentrated on a rotary evaporator at 40° C. to 17 mbar and degassed for 30 minutes at high vacuum to <0.1 mbar at 40° C. The product (compound of formula (I)) was obtained in 57.5% yield of crude product (conversion >99%, selectivity 0.57).

Example 3

In a 100 ml flask equipped with a stirrer, an Argon inlet, dosage inlet, water separator with a water cooled intensive condenser and a bubble counter, 3.35 g (96.7%, 15 mMol, 1.5 eq) of menadiol-1-acetate together with 12 g ethylene carbonate, 15 ml n-heptane and 0.949 mg (99.9%, 2.0 μMol, 0.0002 eq) of $Al(OTf)_3$ were weighed in. Further ~10 ml n-heptane were placed in the separator. Under strong stirring (~1000 rpm) at 100° C., the dosage of 3.23 g (90%, 10 mMol, 1 eq) geranyl geraniol solved in ~2 ml n-heptane over 2 hours was started.

At the same temperature 30 minutes was stirred, then cooled down to 80° C. and add 15 ml n-heptane. The reaction mixture was placed in a separating funnel and separate the lower ethylene carbonate phase. The organic phase is concentrated on a rotary evaporator at 40° C. to 13 mbar and degassed for 30 minutes at high vacuum to <0.1 mbar at 40° C. The product (compound of formula (I)) was obtained in 23.2% yield of crude product (conversion >99%, selectivity 0.23).

The invention claimed is:
1. A process for the production of the compound of formula (I):

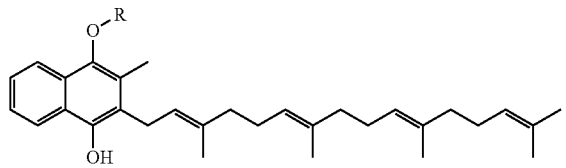
(I)

wherein R is

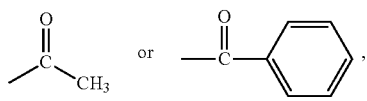

the process comprising reacting a compound of formula (II):

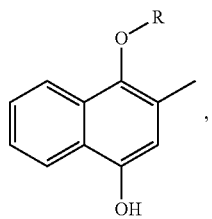
(II)

wherein R is

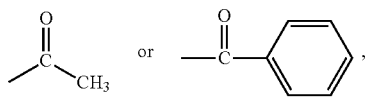

with a compound of formula (III):

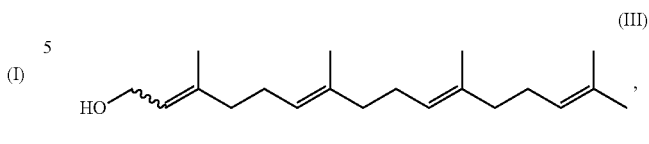
(III)

in the presence of a heterogeneous triflate catalyst which is a compound of formula (IV):

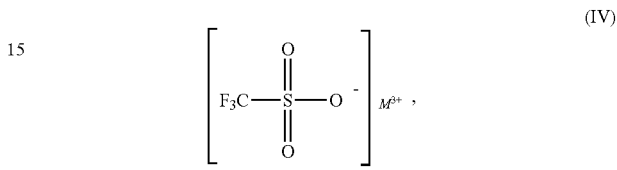
(IV)

wherein M is Al, Bi or Sc.

2. The process according to claim 1, wherein the process is carried out in an inert solvent system.

3. The process according to claim 1, wherein the process is carried out at elevated temperatures.

4. The process according to claim 1, wherein the compounds of formulas (II) and (III) are reacted in equimolar amounts.

5. The process according to claim 1, wherein the compounds of formulas (II) and (III) are present in a molar ratio of the compound of formula (II) to the compound of formula (III) of 1:2 to 2:1.

6. The process according to claim 1, wherein a substrate to catalyst ratio, based on molar amounts of the compound of formula (II) to the catalyst of formula (IV), is from 2000:1 to 50000:1.

7. The process according to claim 6, wherein the substrate to catalyst ratio is from 1500:1 to 30000:1.

8. The process according to claim 1, wherein the process is carried out at an elevated temperature of 30° C. to 150° C.

9. The process according to claim 1, wherein the process achieves >99% conversion of the compounds of formulas (II) and (III).

* * * * *